United States Patent [19]

Mimura et al.

[11] Patent Number: 5,098,887
[45] Date of Patent: Mar. 24, 1992

[54] ANGIOTENSIN CONVERTING ENZYME INHIBITOR

[75] Inventors: Tsutomu Mimura; Yasuhiro Kohama, both of Osaka; Kazuhiko Nagata; Ryoichi Tsurutani, both of Kyoto, all of Japan

[73] Assignee: Unitika Ltd., Hyogo, Japan

[21] Appl. No.: 659,432

[22] Filed: Feb. 26, 1991

[30] Foreign Application Priority Data

Feb. 26, 1990 [JP] Japan .................................. 2-46975

[51] Int. Cl.$^5$ ............................................. C07K 7/06
[52] U.S. Cl. ........................................ 514/15; 514/16; 530/328
[58] Field of Search .................. 530/327, 328; 514/15, 514/16

[56] References Cited

PUBLICATIONS

*Igaku to Seibutsugaku*, vol. 116, p. 159 (1988).

Primary Examiner—Lester L. Lee
Attorney, Agent, or Firm—Sughrue, Mion, Zinn Macpeak & Seas

[57] ABSTRACT

An angiotensin converting enzyme inhibitor containing Gly-Lys-Glu-Ile-Ile-Val-Lys-Ala-Glu-Arg (SEQ ID No: 1) Gly-Lys-Met-Val-Lys-Val-Val-Ser-Trp-Tyr (SEQ ID No: 2) or Ala-Tyr-Ile-Ala-Ser-Lys-Gly-Leu (SEQ ID No: 3) as an active component.

4 Claims, No Drawings

ANGIOTENSIN CONVERTING ENZYME INHIBITOR

FIELD OF THE INVENTION

The invention relates to an angiotensin converting enzyme inhibitor, containing a novel active peptide, which is expected to be useful for the treatment and prevention of hypertension.

BACKGROUND OF THE INVENTION

Angiotensin I, composed of 10 amino acids, is produced through the action of renin, a proteolytic enzyme produced in the kidney, on angiotensinogen present in the serum. Angiotensin converting enzyme acts on angiotensin I releasing a dipeptide from the C-terminus to produce an octapeptide known as angiotensin II which has significant hypertensive activity. Angiotensin converting enzyme is also known to inactivate bradykinin, a substance having hypotensive activity. Accordingly, an angiotensin converting enzyme inhibitor is clinically effective for the prevention and treatment of hypertension.

Conventionally known native substances having angiotensin converting enzyme inhibitory activity include venom peptides and analogues thereof, peptides obtained by treating milk casein with trypsin, as described in JP-B-60-23085, JP-B-60-23086 and JP-B-61-51562 (the term "JP-B" as used herein means an "examined published Japanese patent application"), and peptides extracted from the tissue of fishes, as described in JP-A-1-313498 (the term "JP-A" as used herein means an "unexamined published Japanese patent application") (corresponding to EP-A-345778). Further, it has been reported that an extract of lactic acid bacteria contains a substance having angiotensin converting enzyme inhibitory activity (*Igaku to Seibutsugaku*, Vol. 116, p. 159 (1988)). However, these known angiotensin converting enzyme inhibitors have disadvantages, such as a need for enzymatic treatment with, for example, trypsin, and difficulty in culturing microorganisms.

SUMMARY OF THE INVENTION

An object of the present invention is to provide a naturally-occurring angiotensin converting enzyme inhibitor through an easy cultivation technique and a simple purification scheme without complicated enzymatic treatments.

As a result of extensive investigations, the inventors have found that a hydrolysis mixture of a cell extract of *Bacillus stearothermophilus*, a thermophilic bacterium, contains a few substances having angiotensin converting enzyme inhibitory activity. The substances were identified as oligopeptides.

A first embodiment of the present invention relates to an angiotensin converting enzyme inhibitor comprising Gly-Lys-Glu-Ile-Ile-Val-Lys-Ala-Glu-Arg (SEQ ID No: 1) as an active component.

A second embodiment of the present invention relates to an angiotensin converting enzyme inhibitor comprising Gly-Lys-Met-Val-Lys-Val-Val-Ser-Trp-Tyr (SEQ ID No: 2) as an active component.

A third embodiment of the present invention relates to an angiotensin converting enzyme inhibitor comprising Ala-Tyr-Ile-Ala-Ser-Lys-Gly-Leu (SEQ ID No:3) as an active component.

DETAILED DESCRIPTION OF THE INVENTION

The peptides which are active components of the angiotensin converting enzyme inhibitors according to the present invention can be obtained by treating an extract of microbial cells or through chemical peptide synthesis.

Where the peptides are obtained from microbial cells, microorganisms which can be used include those belonging to the genus Bacillus, Clostridium, Leuconostoc and Streptococcus. Those belonging to the genus Bacillus are preferred from the viewpoint of ease in continuous culturing whereby cells are readily obtained.

The microbial cells can be obtained either from a batch system or from a continuous system.

An extract of the microbial cells can be obtained by treating the cells with a surface active agent, an enzyme (e.g., lysozyme) or a chemical (e.g., ethylenediaminetetraacetic acid (EDTA)); a mechanical method, such as applying pressure, grinding with glass beads, repeated freezing and thawing and treating with ultrasound; or a method utilizing autolysis of the cells. The method utilizing autolysis is preferred particularly because of operating convenience and low cost.

The thus obtained extract is treated by, for example, heating the extract together with an acid, e.g., acetic acid, hydrochloric acid or trifluoroacetic acid, to conduct hydrolysis for a predetermined period of time. The hydrolysis is carried out preferably by using a mixture of acetic acid and hydrochloric acid. In this case, acetic acid and hydrochloric acid are used in concentrations of from 0.01 to 10M and from 1 to 100 mM, respectively, and the hydrolysis temperature preferably ranges from 50° to 150° C.

The resulting hydrolysis product may be used either as crude or as purified. Purification of the hydrolysis product can be performed by column chromatography using ion exchange resins, hydrophobic resins, porous resins etc., countercurrent distribution, electrophoresis, or the like technique.

There are thus obtained at least the above-described three species of peptides with angiotensin converting enzyme inhibitory activity.

A preferred embodiment of the above-described preparation procedures is explained below in more detail.

A strain of *Bacillus stearothermophilus*. e.g., NCA 1503 (ATCC 29609), UK 788 (Ferm BP-2373), UK 563 (Ferm P-7275), ATCC 7953, ATCC 8005, and ATCC 10149, is cultured continuously and the resulting microbial cells are allowed to undergo autolysis to obtain an extract. The extract then is hydrolyzed in a mixed acid solution of 1M acetic acid and 20 mM hydrochloric acid at 120° C. for 1 hour.

The desired peptide can be isolated from the acid hydrolysate and purified by various column chromatographic means, such as column chromatography using a column packed with an ion exchange resin, e.g., Amberlite IRC-50 (produced by Rohm & Haas) or Dowex NWC-1 (produced by Dow Chemical Co.); gel column chromatography using a column packed with Sephadex G-25 (produced by Pharmacia Co.) or Asahi Pack GS-320 (produced by Asahi Chemical Industry Co., Ltd.); and high performance liquid chromatography (HPLC) using a column packed with Asahi Pack ODP-50 (produced by Asahi Chemical Industry Co., Ltd.) or Microbonda-Pack (produced by Waters Co.). Other means commonly employed for purifying peptide compounds, such as counter-current distribution and electrophoresis, can also be utilized.

The peptides according to the present invention can also be synthesized by a well-known liquid phase or solid phase process (as described, for example, in *Pharmacia Review*, Vol. 3, pp 27–47 (1980)) which comprises condensing an amino acid whose amino group is blocked with a protective group, e.g., a benzyloxycarbonyl group or a t-butoxycarbonyl group, with an amino acid or peptide whose carbonyl group is blocked with a protective group, e.g., a benzyl ester group, in the presence of N,N'-dicyclohexylcarbodiimide (DDC) etc. to form a peptide linkage and removing the amino-protective group. Stepwise elongation of the peptide occurs by repeating the process using selected blocked amino acids.

The peptides according to the present invention are formulated in a usual manner into preparations for oral administration, such as tablets, capsules or granules, together with pharmaceutically acceptable carriers, vehicles, binders and other additives or into intravenously injectable preparations including solutions and lyophilized powders which are to be dissolved on use.

A suitable dose of the peptides is usually from 0.001 to 0 mg/kg-b.w. of an animal per day in a single dose or in 2 to 4 divided doses.

The angiotensin converting enzyme inhibitors of the present invention are applicable to mammals having endogenous angiotensin, such as humans, rats and dogs.

The present invention is now illustrated in greater detail with reference to Examples, but it should be understood that the present invention is not deemed to be limited thereto.

REFERENCE EXAMPLE 1

Determination of Angiotensin Converting Enzyme Inhibitory Activity

Angiotensin converting enzyme inhibitory activity during isolation and purification was determined using the method of Cushmann et al., *Biochem. Pharacol.*, Vol. 20, pp. 1637–1648 (1971).

(i) Preparation of Angiotensin Converting Enzyme

A commercially available acetone-dried preparation of rabbit lungs (product of Sigma Co.) was dissolved in a 50 mM potassium phosphate buffer solution (pH=8.3) at 4° C. and the solution was centrifuged at 37,000×g for 30 minutes. The supernatant was dialyzed against the same buffer to remove low-molecular weight substances resulting in an angiotensin converting enzyme solution.

(ii) Determination of Angiotensin Converting Enzyme Inhibitory Activity

Hippuryl-L-histidine-L-leucine (product of Peptide Kenkyusho) was added to a 0.1M potassium phosphate buffer solution (pH=8.3) containing 0.3M NaCl to prepare a 2.5 mM enzyme substrate solution. The above-prepared angiotensin converting enzyme, water and a test sample were added to the substrate solution in a final volume of 0.25 ml and the system was allowed to react at 37° C. for 30 minutes. Then, 0.25 ml of 1N HCl was added thereto to stop the reaction and 1.5 ml of ethyl acetate was added to extract released hippuric acid. A 1 ml aliquot of the ethyl acetate extract was evaporated to dryness. To the residue was added 1 ml of distilled water and the absorbance at 228 nm was measured to determine the amount of hippuric acid.

Percent inhibition was calculated from the above-measured absorbance (A) and an absorbance of a blank (B) according to the following equation:

$$\text{Percent Inhibition (\%)} = \frac{B - A}{B} \times 100$$

The concentration of the sample showing 50% inhibition was taken as $IC_{50}$.

EXAMPLE 1

Isolation and Purification of Peptide from *Bacillus Stearothermophilus*

*Bacillus stearothermophilus* strain NCA-1503 (ATCC 29609) was inoculated in 400 l of medium containing 0.35% (by weight, hereinafter the same) of glucose, 0.30% of a yeast extract 0.10% of peptone, 0.20% of monopotassium phosphate, 0.20% of disodium phosphate, 0.10% of magnesium sulfate, 0.005% of ferrous sulfate, 0.0001% of manganese sulfate and 0.0001% of sodium molybdate and cultured at 60° C. t a pH of 7. The culture was centrifuged to collect the cells, which were then lyophilized for preservation.

The resulting lyophilized cells were suspended in 25 mM potassium phosphate buffer solution (pH'7.6) containing 1M glucose and 4 mM EDTA. The suspension was allowed to stand at 40° C. for 3 hours and then the cell suspension was centrifuged to obtain an aqueous extract.

To a 1 l aliquot of the extract was added 60 ml of acetic acid and 2 ml of concentrated hydrochloric acid and the mixture was heated in an autoclave at 120° C. for 1 hour. After centrifugal separation, 10 g of ODS resin (diameter: 55 to 105 μm; product of Whatman Co.) was added to the supernatant followed by stirring for 1 hour. The resin was collected by filtration, washed with 1 l of 4% acetic acid and eluted with a 15% acetonitrile aqueous solution. The eluent was dried to a solid and the residue was dissolved in a developing solvent for HPLC comprising a 50 mM mixed solution of ammonium acetate and acetonitrile (80:20 by volume). The solution was passed through a column of Asahi Pack GS-320 (product of Asahi Chemical Industry Co., Ltd.; 0.76×80 cm) at a flow rate of 1 ml/min. A 13 to 14 ml-fraction (hereinafter referred to fraction I), a 15 to 16 ml-fraction (hereinafter referred to fraction II) and a 23 to 26 ml-fraction (hereinafter referred to faction III) were found to have inhibitory activity.

Each of active fractions I, II and III was concentrated. The fraction I or II concentrate was purified by HPLC using a column of Develosil ODS-7 (product of Nomura Kagaku K.K.; 0.46×25 cm) using 0.05% hydrochloric acid aqueous solution containing acetonitrile at a straight gradient of from 5% to 30%. The flow rate was 2 ml/min. Inhibitory activity was observed in a 18 to 20 ml-fraction of fraction I and a 22 to 24 ml-fraction of fraction II.

On the other hand, fraction III was purified in the same manner as described above, except for changing the acetonitrile concentration to a gradient of from 10% to 50%. Inhibitory activity was observed in a 21 to 23 ml-fraction.

Each of the resulting three kinds of inhibitory substances was analyzed with a gaseous phase protein sequenator ("Model 470A" manufactured by Applied Biosystems Co.) and was found to respectively have the following amino acid sequence:

(a) Gly-Lys-Glu-Ile-Ile-Val-Lys-Ala-Glu-Arg (SEQ ID No: 1)
(b) Gly-Lys-Met-Val-Lys-Val-Val-Ser-Trp-Tyr (SEQ ID No: 2)
(c) Ala-Tyr-Ile-Ala-Ser-Lys-Gly-Leu (SEQ ID No: 3)

The peptides (a), (b) and (c) were found to have an $IC_{50}$ of 75.1 μg/ml, 8.0 μg/ml, and 28.8 μg/ml, respectively.

While the invention has been described in detail and with reference to specific examples thereof, it will be apparent to one skilled in the art that various changes and modifications can be made therein without departing from the spirit and scope thereof.

What is claimed is:

1. An isolated angiotensin converting enzyme inhibitor having the sequence: Gly-Lys-Glu-Ile-Ile-Val-Lys-Ala-Glu-Arg (SEQ ID No: 1).

2. An isolated angiotensin converting enzyme inhibitor having the sequence: Gly-Lys-Met-Val-Lys-Val-Val-Ser-Trp-Tyr (SEQ ID No: 2).

3. An isolated angiotensin converting enzyme inhibitor having the sequence: Ala-Tyr-Ile-Ala-Ser-Lys-Gly-Leu (SEQ ID No: 3).

4. A therapeutic composition comprising a pharmaceutically effective amount of a peptide selected from the group consisting of:
(a) Gly-Lys-Glu-Ile-Ile-Val-Lys-Ala-Glu-Arg (SEQ ID No: 1);
(b) Gly-Lys-Met-Val-Lys-Val-Val-Ser-Trp-Tyr (SEQ ID No: 2); and
(c) Ala-Tyr-Ile-Ala-Ser-Lys-Gly-Leu (SEQ ID No: 3); and a pharmaceutically acceptable carrier, diluent or excipient.

* * * * *

SEQUENCE LISTING (1) GENERAL INFORMATION:
  (i) APPLICANT:  Mimura, Tsutomu
                  Kohama, Yasuhiro
                  Nagata, Kazuhiko
                  Tsurutani, Ryoichi
  (ii) TITLE OF INVENTION: ANGIOTENSIN CONVERTING ENZYME INHIBITOR
  (iii) NUMBER OF SEQUENCES: 3
  (iv) CORRESPONDENCE ADDRESS:
      (A) ADDRESSEE: Sughrue, Mion, Zinn, Macpeak & Seas
      (B) STREET: 2100 Pennsylvania Avenue
      (C) CITY: Washington
      (D) STATE: D.C.
      (E) COUNTRY: U.S.A.
      (F) ZIP: 20037-3202
  (v) COMPUTER READABLE FORM:
      (A) MEDIUM TYPE: Floppy disk
      (B) COMPUTER: IBM PC compatible
      (C) OPERATING SYSTEM: PC-DOS/MS-DOS
      (D) SOFTWARE: PatentIn Release #1.24
  (vi) CURRENT APPLICATION DATA:
      (A) APPLICATION NUMBER: US
      (B) FILING DATE:
      (C) CLASSIFICATION:
  (vii) PRIOR APPLICATION DATA:
      (A) APPLICATION NUMBER: JP 02-46975
      (B) FILING DATE: 26-FEB-1990
  (ix) TELECOMMUNICATION INFORMATION:
      (A) TELEPHONE: (202)293-7060
      (B) TELEFAX: (202)293-7860
      (C) TELEX: 6491103

(2) INFORMATION FOR SEQ ID NO:1:
  (i) SEQUENCE CHARACTERISTICS:
      (A) LENGTH: 10 amino acids
      (B) TYPE: amino acid

-continued
SEQUENCE LISTING (D) TOPOLOGY: linear
  (ii) MOLECULE TYPE: peptide
  (vi) ORIGNAL SOURCE:
      (A) ORGANISM: *Bacillus stearothermophilus*
      (B) STRAIN: NCA-1503
  (xi) SEQUENCE DESCRIPTION: SEQ ID NO:1:

Gly Lys Glu Ile Ile Val Lys Ala Glu Arg
1               5                   10

(2) INFORMATION FOR SEQ ID NO:2:
  (i) SEQUENCE CHARACTERISTICS:
      (A) LENGTH: 10 amino acids
      (B) TYPE: amino acid
      (D) TOPOLOGY: linear
  (ii) MOLECULE TYPE: peptide
  (vi) ORIGINAL SOURCE:
      (A) ORGANISM: *Bacillus stearothermophilus*
      (B) STRAIN: NCA-1503
  (xi) SEQUENCE DESCRIPTION: SEQ ID NO:2:

Gly Lys Met Val Lys Val Val Ser Trp Tyr
1               5                   10

(2) INFORMATION FOR SEQ ID NO:3:
  (i) SEQUENCE CHARACTERISTICS:
      (A) LENGTH: 8 amino acids
      (B) TYPE: amino acid
      (D) TOPOLOGY: linear
  (ii) MOLECULE TYPE: peptide
  (vi) ORIGINAL SOURCE:
      (A) ORGANISM: *Bacillus stearothermophilus*
      (B) STRAIN: NCA-1503
  (xi) SEQUENCE DESCRIPTION: SEQ ID NO:3:

Ala Tyr Ile Ala Ser Lys Gly Leu
1               5